US010172528B2

(12) United States Patent
Bandyopadhyay et al.

(10) Patent No.: US 10,172,528 B2
(45) Date of Patent: Jan. 8, 2019

(54) METHOD AND SYSTEM FOR PHYSIOLOGICAL PARAMETER DERIVATION FROM PULSATING SIGNALS WITH REDUCED ERROR

(71) Applicant: Tata Consultancy Services Limited, Mumbai (IN)

(72) Inventors: Soma Bandyopadhyay, Kolkata (IN); Arijit Ukil, Kolkata (IN); Chetanya Puri, Kolkata (IN); Rituraj Singh, Kolkata (IN); Arpan Pal, Kolkata (IN); C A Murthy, Kolkata (IN); Kayapanda Mandana, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 124 days.

(21) Appl. No.: 15/467,789

(22) Filed: Mar. 23, 2017

(65) Prior Publication Data

US 2017/0340211 A1 Nov. 30, 2017

(30) Foreign Application Priority Data

May 31, 2016 (IN) .............................. 201621018713

(51) Int. Cl.
*A61B 5/04* (2006.01)
*A61B 5/024* (2006.01)
(Continued)

(52) U.S. Cl.
CPC ............ *A61B 5/024* (2013.01); *A61B 5/0002* (2013.01); *A61B 5/0245* (2013.01);
(Continued)

(58) Field of Classification Search
CPC ... A61B 5/0002; A61B 5/02108; A61B 5/024; A61B 5/02405; A61B 5/02416;
(Continued)

(56) References Cited

U.S. PATENT DOCUMENTS

| 8,574,162 B2 | 11/2013 | Watson |
| 9,113,830 B2 | 8/2015 | Galen et al. |
| 2015/0282724 A1* | 10/2015 | McDuff ............. A61B 5/02427 600/479 |

FOREIGN PATENT DOCUMENTS

WO WO 2015/049113 A1 4/2015

OTHER PUBLICATIONS

Couceiro, P. et al., "Detection of motion artifacts in photoplethysmographic signals based on time and period domain analysis" Engineering in Medicine and Biology Society (EMBC), 2012 Annual International Conference of the IEEE., IEEE, (2012).
(Continued)

*Primary Examiner* — George Manuel
(74) *Attorney, Agent, or Firm* — Finnegan, Henderson, Farabow, Garrett & Dunner LLP (57) ABSTRACT

This disclosure relates generally to biomedical signal processing, and more particularly to method and system for physiological parameter derivation from pulsating signals with reduced error. In this method, pulsating signals are extracted, spurious perturbations in the extracted pulsating signals are removed for smoothening, local minima points in the smoothened pulsating signal are derived, systolic maxima point between two derived local minima are derived, most probable pulse duration and most probable peak-to-peak distance are derived, dicrotic minima is removed while ensuring that every dicrotic minima is preceded by a systolic maxima point and followed by a beat start point of said systolic maxima, diastolic peak is derived while ensuring that every dicrotic maxima is preceded by a diastolic notch followed by next beat start point of that maxima, and physiological parameters are derived from the derived local minima points, systolic maxima points, dicrotic notch and diastolic peak.

13 Claims, 3 Drawing Sheets

(51) Int. Cl.
*A61B 5/00* (2006.01)
*A61B 5/0245* (2006.01)
*A61B 5/0402* (2006.01)
*A61B 5/0456* (2006.01)
*A61B 5/046* (2006.01)
*A61B 5/0468* (2006.01)
*A61B 5/021* (2006.01)

(52) U.S. Cl.
CPC ...... *A61B 5/02108* (2013.01); *A61B 5/02405* (2013.01); *A61B 5/02416* (2013.01); *A61B 5/02438* (2013.01); *A61B 5/0402* (2013.01); *A61B 5/046* (2013.01); *A61B 5/0456* (2013.01); *A61B 5/0468* (2013.01); *A61B 5/7203* (2013.01)

(58) Field of Classification Search
CPC . A61B 5/02438; A61B 5/0245; A61B 5/0402; A61B 5/0456; A61B 5/046; A61B 5/0468; A61B 5/7203
See application file for complete search history.

(56) References Cited

OTHER PUBLICATIONS

Kuntamalla, S., "An Efficient and Automatic Systolic Peak Detection Algorithm for Photoplethysmographic Signals", International Journal of Computer Applications, vol. 97, No. 19, pp. 18-23, Jul. 2014.

* cited by examiner

METHOD AND SYSTEM FOR PHYSIOLOGICAL PARAMETER DERIVATION FROM PULSATING SIGNALS WITH REDUCED ERROR

PRIORITY CLAIM

This U.S. patent application claims priority under 35 U.S.C. § 119 to: India Application No. 201621018713, filed on 31 May 2016. The entire contents of the aforementioned application are incorporated herein by reference.

TECHNICAL FIELD

This disclosure relates generally to biomedical signal processing, and more particularly to a method and system for deriving physiological parameters from pulsating signals with reduced error.

BACKGROUND

Huge number of Internet of Things (IoT) devices are available to promote health care management and wellness. It is undoubted that IoT Healthcare solutions can provide remote monitoring to support patients suffering from various diseases and disorders. But, a gamut of expensive sensor devices, sophisticated, periodic setup, maintenance and calibration as well as up-to-date training are required for such purpose to come to fruition. In order to promote widespread usage and affordability, such costly and extensive intricacies do not work positively towards the ubiquity and success of mobile and preventable health care, specifically in developing countries. As a result, deriving various physiological parameters of a person in a noninvasive and affordable manner is a significant task and challenge. Pulsating signals have gained high importance for the purpose of derivation of various physiological parameters of a person. As a result, extracting the various time series features of pulsating signals like photoplethysmogram (PPG) signal and then co-relating them with physiological parameters is a necessity to create noninvasive and affordable healthcare analytics applications.

The inventors here have recognized certain technical problems with such conventional systems, as explained below. In the majority of conventional systems, a pulsating signal like photoplethysmogram (PPG) signal has lot of noise and the analytics to be performed are mostly run on low power battery operated devices like mobile phones. This causes errors and increased resource usage in conventional systems that are being used for deriving various physiological parameters of a person in a noninvasive and affordable manner. Thereby, deriving physiological parameters from pulsating signals with reduced error while requiring low computational power is still considered to be one of the biggest challenges of the technical domain.

SUMMARY

Embodiments of the present disclosure present technological improvements as solutions to one or more of the above-mentioned technical problems recognized by the inventors in conventional systems. For example, in one embodiment, a method for deriving a plurality of physiological parameters from pulsating signals with reduced error for monitoring cardiac health of a patient is provided. The method comprises extracting pulsating signals from the patient, removing spurious perturbations in the extracted pulsating signals using two different time window lengths for smoothening of said extracted pulsating signals, deriving local minima points in the smoothened pulsating signals based on the discrete nature of said pulsating signals and strictly rising and falling edge of said pulsating signals and union of minima points derived from the smoothened pulsating signals with two different sizes, deriving systolic maxima point between two derived local minima based on the discrete nature of said pulsating signals, strictly rising and falling edge of said pulsating signals and union of maxima points derived from the smoothened pulsating signals with two different sizes, deriving most probable pulse duration and most probable peak-to-peak distance using the derived local minima points and the derived systolic maxima points and based on the univariate nature of said pulsating signals, deriving dicrotic minima based on the discrete nature of said pulsating signals, strictly rising and falling edge of said pulsating signals and union of the local minima points derived from two different smoothened pulsating signals with two different sizes ensuring that every dicrotic minima is preceded by a systolic maxima point and followed by a beat start point of said systolic maxima, deriving diastolic peak based on the discrete nature of said pulsating signals, strictly rising and falling edge of said pulsating signals and union of the systolic maxima points derived from two different smoothened pulsating signals with two different sizes ensuring that every dicrotic maxima is preceded by a diastolic notch and followed by next beat start point of that maxima and deriving physiological parameters from the derived local minima points, systolic maxima points, dicrotic notch and diastolic peak.

In another embodiment, a system for deriving a plurality of physiological parameters from pulsating signals for monitoring cardiac health of a patient. The system comprising a signal extraction module adapted for extracting pulsating signals from the patient; a smoothening module adapted for removing spurious perturbations in the extracted pulsating signals using two different time window lengths for smoothening of said extracted pulsating signals; a minima derivation module adapted for deriving local minima points in the smoothened pulsating signals based on the discrete nature of said pulsating signals and strictly rising and falling edge of said pulsating signals and union of minima points derived from the smoothened pulsating signals with two different sizes; a maxima derivation module adapted for deriving systolic maxima point between two derived local minima based on the discrete nature of said pulsating signals, strictly rising and falling edge of said pulsating signals and union of maxima points derived from the smoothened pulsating signals with two different sizes; a statistical learning module adapted for deriving most probable pulse duration and most probable peak-to-peak distance using the derived local minima points and the derived systolic maxima points and based on the univariate nature of said pulsating signals; a dicrotic minima derivation module adapted for deriving dicrotic minima based on the discrete nature of said pulsating signals, strictly rising and falling edge of said pulsating signals and union of the local minima points derived from two different smoothened pulsating signals with two different sizes ensuring that every dicrotic minima is preceded by a systolic maxima point and followed by a beat start point of said systolic maxima; a diastolic peak derivation module adapted for deriving diastolic peak based on the discrete nature of said pulsating signals, strictly rising and falling edge of said pulsating signals and union of the systolic maxima points derived from two different smoothened pulsating signals with two different sizes ensuring that every dicrotic maxima is preceded by a diastolic notch and followed by next beat start point of that maxima; and a physiological parameter derivation module adapted for deriving physiological parameters from the derived local minima points, systolic maxima points, dicrotic notch and diastolic peak.

In yet another embodiment, a Computer Program Product (CPP) for deriving a plurality of physiological parameters from pulsating signals with reduced error for monitoring cardiac health of a patient is provided. Further comprises of extracting pulsating signals from the patient, removing spurious perturbations in the extracted pulsating signals using two different time window lengths for smoothening of said extracted pulsating signals, deriving local minima points in the smoothened pulsating signals based on the discrete nature of said pulsating signals and strictly rising and falling edge of said pulsating signals and union of minima points derived from the smoothened pulsating signals with two different sizes, deriving systolic maxima point between two derived local minima based on the discrete nature of said pulsating signals, strictly rising and falling edge of said pulsating signals and union of maxima points derived from the smoothened pulsating signals with two different sizes, deriving most probable pulse duration and most probable peak-to-peak distance using the derived local minima points and the derived systolic maxima points and based on the univariate nature of said pulsating signals, deriving dicrotic minima based on the discrete nature of said pulsating signals, strictly rising and falling edge of said pulsating signals and union of the local minima points derived from two different smoothened pulsating signals with two different sizes ensuring that every dicrotic minima is preceded by a systolic maxima point and followed by a beat start point of said systolic maxima, deriving diastolic peak based on the discrete nature of said pulsating signals, strictly rising and falling edge of said pulsating signals and union of the systolic maxima points derived from two different smoothened pulsating signals with two different sizes ensuring that every dicrotic maxima is preceded by a diastolic notch and followed by next beat start point of that maxima and deriving physiological parameters from the derived local minima points, systolic maxima points, dicrotic notch and diastolic peak.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The present disclosure provides a method and system for deriving physiological parameters from pulsating signals with reduced error.

In an aspect of the invention, photoplethysmogram (PPG) signals can be used as the pulsating signal. The different features derived from PPG signal can be used to detect various parameters to detect physiological issues in a patient.

In an exemplary aspect, once the pulse peak amplitude (PPA) and the systolic amplitude is derived from the PPG signal, premature ventricular contraction in a patient's body can be detected. The height of AC component of the photoplethysmogram is proportional to the pulse pressure, the difference between the systolic and diastolic pressure in the arteries. The PPG pulse for the cardiac cycle with the PVC results in lower amplitude blood pressure and a PPG. Ventricular tachycardia and ventricular fibrillation can also be detected.

In another exemplary aspect, once the PDT (Pulse Duration Time) amplitude is derived from the PPG signal, heart rate variability (HRV) in a patient's body can be detected. It has been suggested that ratio of pulse interval to its systolic amplitude could provide an understanding of the properties of the patient's cardiovascular system. When the HRV derived using the pulse interval in PPG signals have been compared with the HRV using R-R intervals in ECG signals, the results have demonstrated that HRV in PPG and ECG signals are highly correlated. They strongly suggested that PPG signals could be used as an alternative measurement of HRV.

In another exemplary aspect, once the SDPT (Systolic to diastolic peak difference) is derived from the PPG signal, the Large Artery Stiffness Index in a patient's body can be detected. Time delay between the systolic and diastolic peaks, or, in the absence of a second peak, the point of inflection is related to the transit time of pressure waves from the root of the subclavian artery to the apparent site of reflection and back to the subclavian artery. This path length can be assumed to be proportional to subject height.

Figure 1:
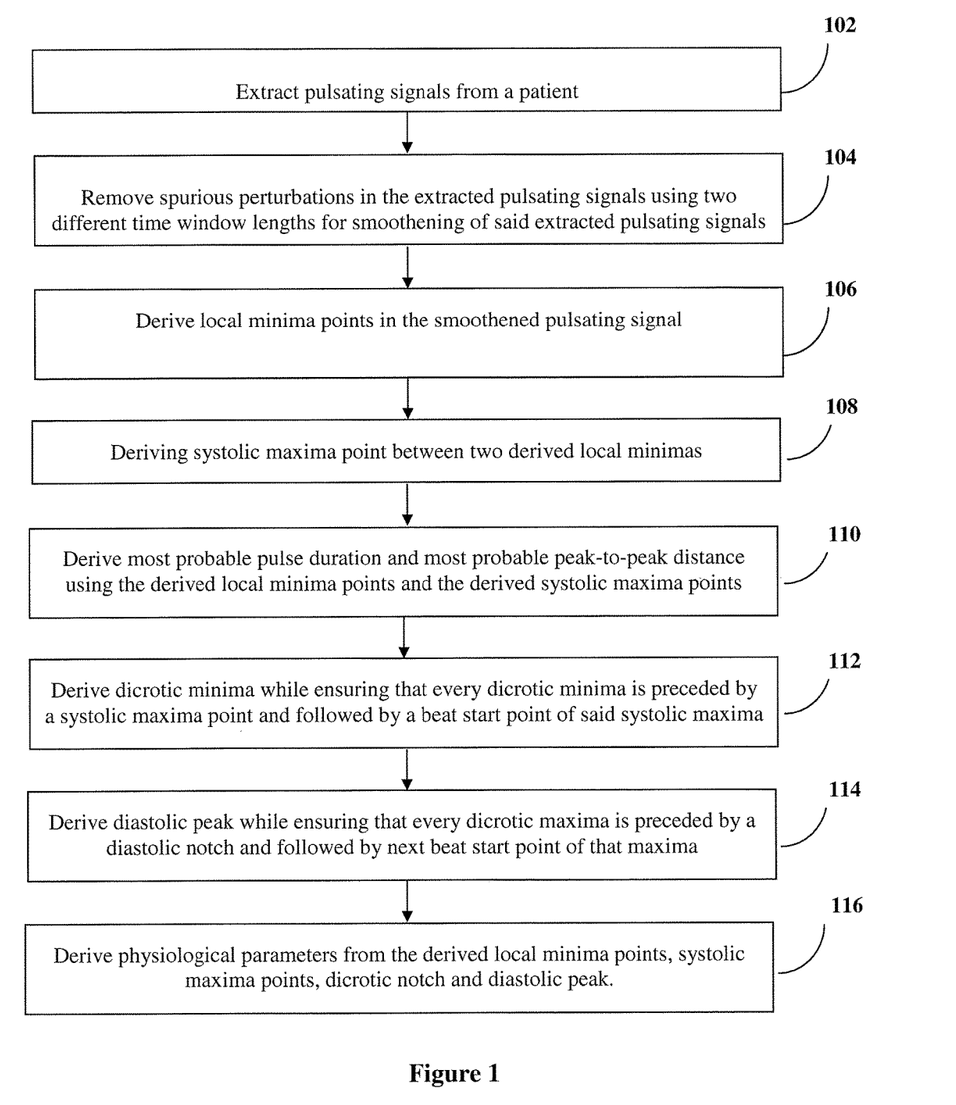
FIG. 1 is a flow chart illustrating method for physiological parameter derivation from pulsating signal with reduced error, according to some embodiments of the present disclosure.

FIG. 1 is a flow chart illustrating method for physiological parameter derivation from pulsating signal with reduced error, according to some embodiments of the present disclosure. The process starts at step 102, pulsating signals are extracted from a patient. At the step 104, spurious perturbations in the extracted pulsating signals are removed. At step 106, local minima points are derived in the smoothened pulsating signal. At step 108, systolic maxima point between two derived local minima are derived. At step 110, most probable pulse duration and most probable peak-to-peak distance are derived using the derived local minima points and the derived systolic maxima points. At step 112, dicrotic minima is derived while ensuring that every dicrotic minima is preceded by a systolic maxima point and followed by a beat start point of said systolic maxima. At step 114, diastolic peak is derived while ensuring that every dicrotic maxima is preceded by a diastolic notch and followed by next beat tart point of that maxima and at step 116, physiological parameters are derived from the derived local minima points, systolic maxima points, dicrotic notch and diastolic peak.

Figure 2:
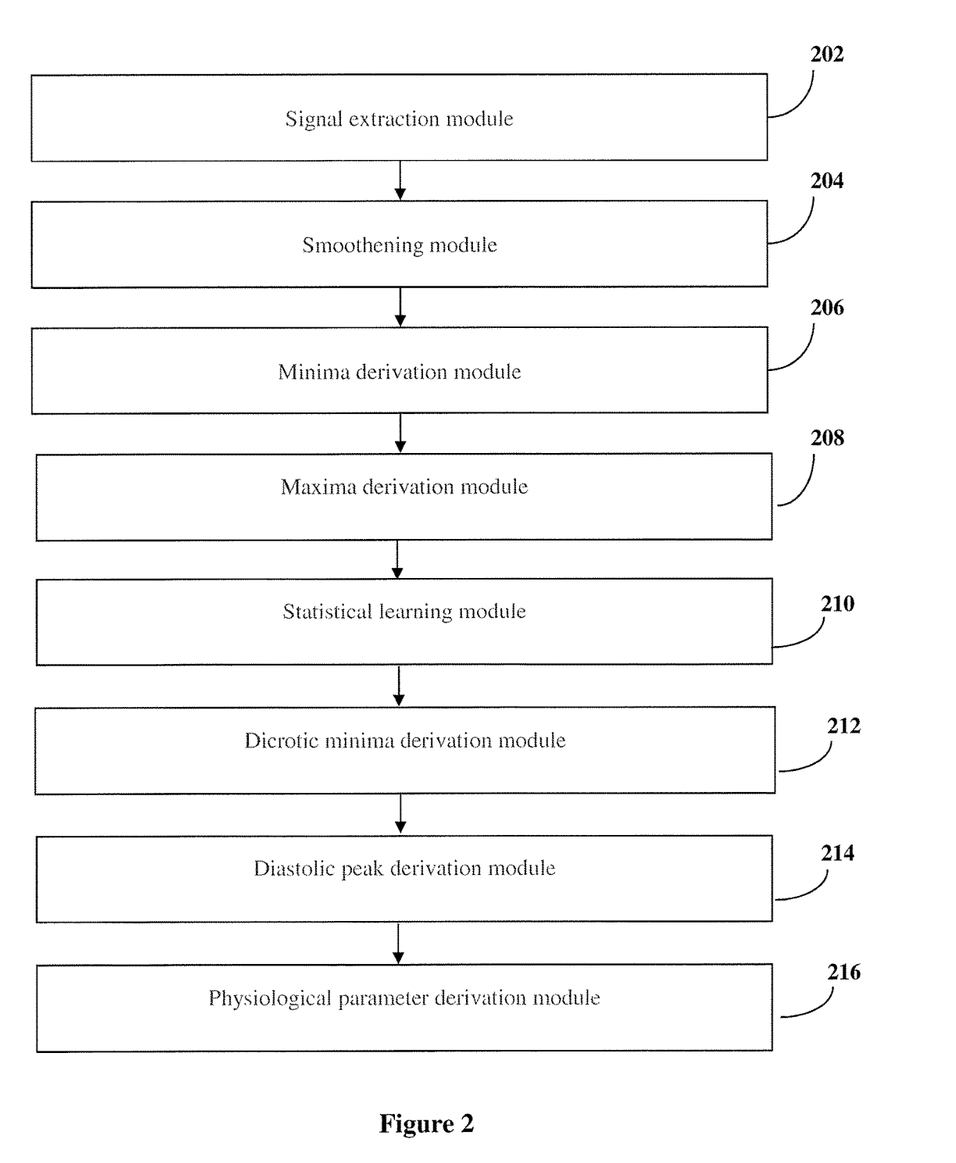
FIG. 2 illustrates an exemplary block diagram of a system for physiological parameter derivation from pulsating signal with reduced error, according to some embodiments of the present disclosure.

FIG. 2 illustrates an exemplary block diagram of a system for physiological parameter derivation from pulsating signal with reduced error, according to some embodiments of the present disclosure.

In an embodiment of the present invention, the system 200 for deriving a plurality of physiological parameters from pulsating signals with reduced error for monitoring cardiac health of a patient comprises of a signal extraction module 202, a smoothening module 204, a minima derivation module 206, a maxima derivation module 208, a statistical learning module 210, a dicrotic minima derivation module 212, a diastolic peak derivation module 214 and a physiological parameter derivation module 216.

The method described herein is applicable for any pulsating signals. The method derives various time series and signal properties and co-relates them with various physiological parameters. It indicates physiological abnormality in a noninvasive way and performs analytics with reduced errors and optimized resource usage. Thus, in an exemplary embodiment, the applicable pulsating signal is selected from photoplethysmogram (PPG) signals and arterial blood pressure (ABP) signals.

In another embodiment of the present invention, the signal extraction module 202 consists of a mobile communication device or a wearable device. In an exemplary embodiment of the present invention, wherein photoplethysmogram (PPG) signal is used as the pulsating signal, an image capturing device is coupled with the mobile communication device for extracting photoplethysmogram (PPG) signals from the patient. The photoplethysmogram (PPG) signals are extracted from patient's peripheral body parts selected from a group comprising but not limited to finger, ear, forehead and toe. The mobile communication device captures photoplethysmogram signal in reflective mode and the mobile communication device is selected from a group comprising of smart phone, mobile phone, laptop, tablet, and personal digital assistant. The image capturing device coupled with the mobile communication device is a camera and has a light emitting source for extracting photoplethysmogram signals from the patient's peripheral body parts selected from a group comprising but not limited to finger, ear, toe, and forehead; thereby obtaining a video sequence of the light, reflected from patient's peripheral body parts.

In another embodiment of the present invention, in the smoothening module 204, spurious perturbations in the extracted pulsating signals are removed by using two different time window lengths for smoothening of said extracted pulsating signals. Smoothening is performed to remove inequalities in the said extracted pulsating signals by taking union of two MA (moving average) windows (MA=5 and MA=7) instead of a single window, in accordance with FIG. 3.

Figure 3:
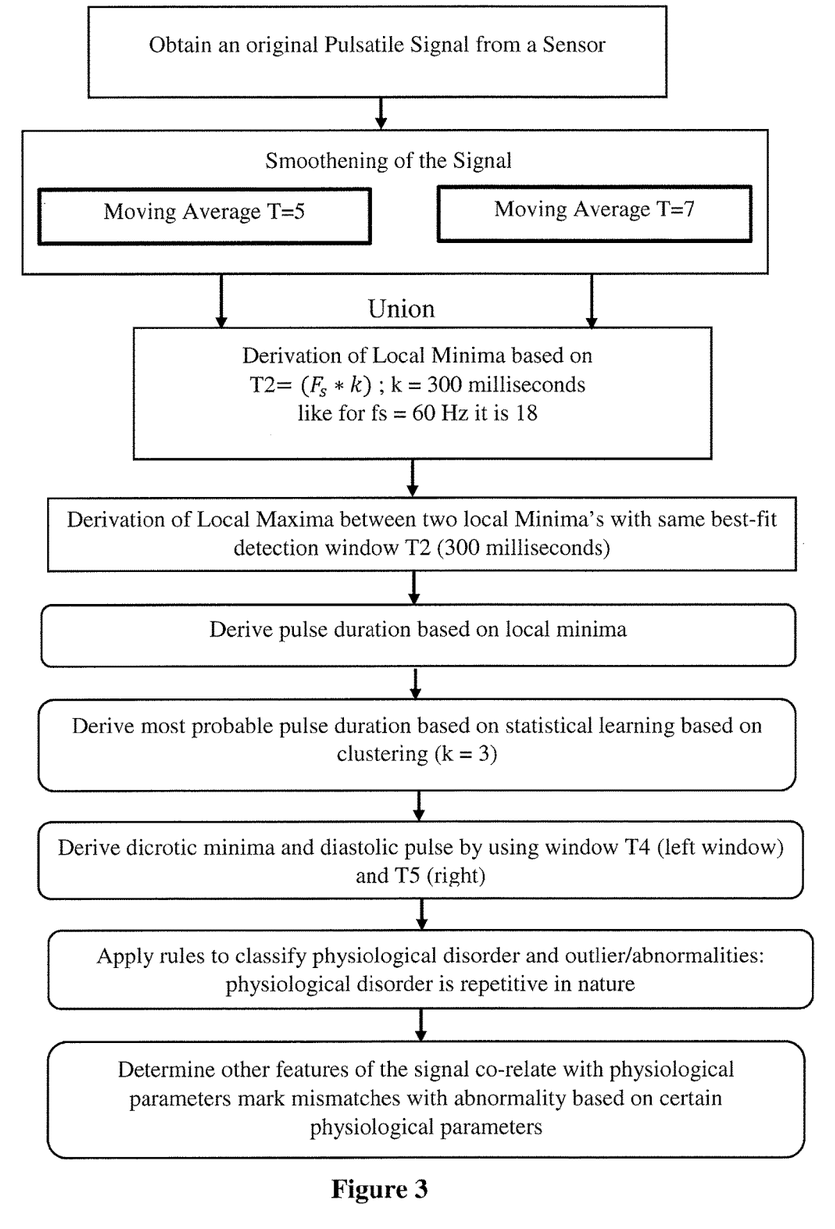
FIG. 3 illustrates an exemplary embodiment of physiological parameter derivation from pulsating signal with reduced error, in accordance with some embodiments of the present disclosure.

Signals with union operation after MA (moving average):
S1=X1, X2 . . . XM; set of Local Minima obtained taking T1=5
S2=Y1, Y2 . . . YN; set of Local Minima obtained taking T1=7
S=S1 U S2
Arranging S in increasing order:

If ($|a_i - a_{i+1}| <= 2$)
{
    Replace both points ($a_i$, $a_{i+1}$) by (($a_i + a_{i+1}$)/2)
}

In another embodiment of the present invention, in the minima derivation module 206, local minima points are derived in the smoothened pulsating signals based on the discrete nature of said pulsating signals and strictly rising and falling edge of said pulsating signals and union of minima points derived from the smoothened pulsating signals with two different window sizes, in accordance with FIG. 3. Derivation of Local Minima is based T2=($F_s$*k); k=300 milliseconds. Mathematical equations to derive local minima are given below:

$$Y_{r0-10} > Y_{r0-r9} > \ldots > Y_{r0} < Y_{r0+1} < \ldots < Y_{r0+10} \quad (1)$$

Consecutive local minima's $|Y_{tn}-1-Y_{tn}| > T3$; T3=($F_s$*k); k=300 milliseconds where T3 denotes the threshold.

The local minima is derived by using the following method:
Input:
T2: Window size
T3: Distance between two minima
$\check{D}_{MA}$: Smoothed signal $x_k$ with k=1, 2, 3, . . . N; N: length(D)
Output: MI: Minima location.
M: =Detecting Indices of $\tilde{D}$ such that:

$$\tilde{x}_{k-\frac{T2}{2}} > \tilde{x}_{k-\frac{T2}{2}+1} \ldots > \tilde{x}_{k-1} > \tilde{x}_k < \tilde{x}_{k+1} \ldots < \tilde{x}_{k+\frac{T2}{2}} \quad (2)$$

MI: =Discard indices $M_k$ in M such that $|M_k - M_{k-1}| < T3$

In another embodiment of the present invention, in the maxima derivation module 208, systolic maxima point between two derived local minima are derived based on the discrete nature of said pulsating signals, strictly rising and falling edge of said pulsating signals and union of maxima points derived from the smoothened pulsating signals with two different window sizes instead of one window as used in the traditional methods, in accordance with FIG. 3. The derivation of Local Maxima based on deriving a local maxima between two local minima with same best-fit detection window T2 (300 milliseconds). The systolic maxima point between two derived local minima points is derived and similar steps are performed as obtaining local minima points to result in the final set of systolic maxima points.

In another embodiment of the present invention, in the statistical learning module 210, most probable pulse duration and most probable peak-to-peak distance are derived using the derived local minima points and the derived systolic maxima points, in accordance with FIG. 3. The said derivation of most probable pulse duration and most probable peak-to-peak distance is based on the univariate nature of said pulsating signals. In this module, first pulse duration is derived based on local minima. Next, most probable pulse duration is derived based on statistical learning based on clustering (k=3) while exploiting the uni-dimensional nature of the signal.

In another embodiment of the present invention, in the dicrotic minima derivation module 212, dicrotic minima is derived based on the discrete nature of said pulsating signals, strictly rising and falling edge of said pulsating signals and union of the local minima points derived from two different smoothened pulsating signals with two different sizes ensuring that every dicrotic minima is preceded by a systolic maxima point and followed by a beat start point of said systolic maxima. The following method is followed for dicrotic minima derivation:

Function p=Detect dicrotic minima
Input: $\varphi_{min}, \varphi_{max}$:
$win_l$: Window size on the left
$win_r$: Window size on the right
$\tilde{D}_{MA}$: Smoothed signal $x_k$ with k=1, 2, 3, ... N; N: length
($D_{\varphi_{min}}$: Final set of minima obtained
Output:
DI: Dicrotic indices $$M_{dc}\text{:Find indices of } \tilde{D} \text{ such that: } \tilde{x}_{k-win_l} > \tilde{x}_{k-win_l+1} \cdots < \tilde{x}_{k-1} > \tilde{x}_k < \tilde{x}_{k+1} \cdots < \tilde{x}_{k+win_r} \quad (3)$$

$M'_{dc}$: =Filter $M_{dc}$ to ensure that every dicrotic minima is preceded by a maxima in $\varphi_{max}$ and followed by the next minima in $\varphi_{min}$ of that maxima.

$$DI = M'_{dc} - \varphi_{min} \quad (4)$$

In another embodiment of the present invention, in the diastolic peak derivation module 214, diastolic peak is derived based on the discrete nature of said pulsating signals, strictly rising and falling edge of said pulsating signals and union of the systolic maxima points derived from two different smoothened pulsating signals with two different sizes ensuring that every dicrotic maxima is preceded by a diastolic notch and followed by next beat start point of that maxima. Every diastolic peak should be situated between a dicrotic minima and the immediately following minima point and derived by using the similar steps as in dicrotic minima points.

In another embodiment of the present invention, in the physiological parameter derivation module 216, physiological parameters are derived from the derived local minima points, systolic maxima points, dicrotic notch and diastolic peak. The physiological parameter derivation module 216 further consists of marking physiological abnormalities based on the derived physiological parameters and the marking of physiological abnormalities is performed using a predefined set of rules. The predefined set of rules is used to classify between abnormalities arising out of physiological parameter disorder and anomaly outliers, wherein the physiological parameter disorders are repetitive in nature.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method for deriving a plurality of physiological parameters from pulsating signals for monitoring cardiac health of a patient, said method comprising:

extracting, via one or more hardware processors, pulsating signals from the patient using a signal extraction module;

removing, via one or more hardware processors, spurious perturbations in the extracted pulsating signals using two different time window lengths for smoothening of said extracted pulsating signals, by using a smoothening module;

deriving, via one or more hardware processors, local minima points in the smoothened pulsating signals based on the discrete nature of said pulsating signals and strictly rising and falling edge of said pulsating signals and union of minima points derived from the smoothened pulsating signals with two different sizes using a minima derivation module;

deriving, via one or more hardware processors, systolic maxima point between two derived local minima based on the discrete nature of said pulsating signals, strictly rising and falling edge of said pulsating signals and union of maxima points derived from the smoothened pulsating signals with two different sizes using a maxima derivation module;

deriving, via one or more hardware processors, most probable pulse duration and most probable peak-to-peak distance using the derived local minima points and the derived systolic maxima points and based on the univariate nature of said pulsating signals by using a statistical learning module;

deriving, via one or more hardware processors, dicrotic minima based on the discrete nature of said pulsating signals, strictly rising and falling edge of said pulsating signals and union of the local minima points derived from two different smoothened pulsating signals with two different sizes ensuring that every dicrotic minima is preceded by a systolic maxima point and followed by a beat start point of said systolic maxima by using a dicrotic minima derivation module;

deriving, via one or more hardware processors, diastolic peak based on the discrete nature of said pulsating signals, strictly rising and falling edge of said pulsating signals and union of the systolic maxima points derived from two different smoothened pulsating signals with two different sizes ensuring that every dicrotic maxima is preceded by a diastolic notch and followed by next beat start point of that maxima by using a diastolic peak derivation module; and deriving, via one or more hardware processors, physiological parameters from the derived local minima points, systolic maxima points, dicrotic notch and diastolic peak using a physiological parameter derivation module.

2. The method as claimed in claim 1, wherein said pulsating signals are selected from photoplethysmogram (PPG) signals and arterial blood pressure (ABP) signals.

3. The method as claimed in claim 1, wherein the signal extraction module consists of a mobile communication device or a wearable device.

4. The method as claimed in claim 1, wherein the smoothening of the extracted pulsating signals is performed by taking union of two moving average windows.

5. The method as claimed in claim 1, wherein the derivation of local minima points in the smoothened pulsating signals is a time window based process.

6. The method as claimed in claim 1, wherein the derivation of best fit window is used as 300 milliseconds.

7. The method as claimed in claim 1, wherein the derivation of systolic maxima between two derived local minima is a time window based process.

8. The method as claimed in claim 1 further consists of marking physiological abnormalities based on the derived physiological parameters.

9. The method as claimed in claim 8, wherein said marking of physiological abnormalities is performed using a predefined set of rules.

10. The method as claimed in claim 9, the predefined set of rules is used to classify between abnormalities arising out of physiological parameter disorder and anomaly outliers.

11. The method as claimed in claim 10, the physiological parameter disorders are repetitive in nature.

12. A system for deriving a plurality of physiological parameters from pulsating signals for monitoring cardiac health of a patient; said system comprising:
    a signal extraction module adapted for extracting pulsating signals from the patient;
    a smoothening module adapted for removing spurious perturbations in the extracted pulsating signals using two different time window lengths for smoothening of said extracted pulsating signals;
    a minima derivation module adapted for deriving local minima points in the smoothened pulsating signals based on the discrete nature of said pulsating signals and strictly rising and falling edge of said pulsating signals and union of minima points derived from the smoothened pulsating signals with two different sizes;
    a maxima derivation module adapted for deriving systolic maxima point between two derived local minima based on the discrete nature of said pulsating signals, strictly rising and falling edge of said pulsating signals and union of maxima points derived from the smoothened pulsating signals with two different sizes;
    a statistical learning module adapted for deriving most probable pulse duration and most probable peak-to-peak distance using the derived local minima points and the derived systolic maxima points and based on the univariate nature of said pulsating signals;
    a dicrotic minima derivation module adapted for deriving dicrotic minima based on the discrete nature of said pulsating signals, strictly rising and falling edge of said pulsating signals and union of the local minima points derived from two different smoothened pulsating signals with two different sizes ensuring that every dicrotic minima is preceded by a systolic maxima point and followed by a beat start point of said systolic maxima;
    a diastolic peak derivation module adapted for deriving diastolic peak based on the discrete nature of said pulsating signals, strictly rising and falling edge of said pulsating signals and union of the systolic maxima points derived from two different smoothened pulsating signals with two different sizes ensuring that every dicrotic maxima is preceded by a diastolic notch and followed by next beat start point of that maxima; and
    a physiological parameter derivation module adapted for deriving physiological parameters from the derived local minima points, systolic maxima points, dicrotic notch and diastolic peak.

13. A computer program product for deriving a plurality of physiological parameters from pulsating signals for monitoring cardiac health of a patient, comprising:
    extracting, via one or more hardware processors, pulsating signals from the patient using a signal extraction module;
    removing, via one or more hardware processors, spurious perturbations in the extracted pulsating signals using two different time window lengths for smoothening of said extracted pulsating signals, by using a smoothening module;
    deriving, via one or more hardware processors, local minima points in the smoothened pulsating signals based on the discrete nature of said pulsating signals and strictly rising and falling edge of said pulsating signals and union of minima points derived from the smoothened pulsating signals with two different sizes using a minima derivation module;
    deriving, via one or more hardware processors, systolic maxima point between two derived local minima based on the discrete nature of said pulsating signals, strictly rising and falling edge of said pulsating signals and union of maxima points derived from the smoothened pulsating signals with two different sizes using a maxima derivation module;
    deriving, via one or more hardware processors, most probable pulse duration and most probable peak-to-peak distance using the derived local minima points and the derived systolic maxima points and based on the univariate nature of said pulsating signals by using a statistical learning module;
    deriving, via one or more hardware processors, dicrotic minima based on the discrete nature of said pulsating signals, strictly rising and falling edge of said pulsating signals and union of the local minima points derived from two different smoothened pulsating signals with two different sizes ensuring that every dicrotic minima is preceded by a systolic maxima point and followed by a beat start point of said systolic maxima by using a dicrotic minima derivation module;
    deriving, via one or more hardware processors, diastolic peak based on the discrete nature of said pulsating signals, strictly rising and falling edge of said pulsating signals and union of the systolic maxima points derived from two different smoothened pulsating signals with two different sizes ensuring that every dicrotic maxima is preceded by a diastolic notch and followed by next beat start point of that maxima by using a diastolic peak derivation module; and deriving, via one or more hardware processors, physiological parameters from the derived local minima points, systolic maxima points, dicrotic notch and diastolic peak using a physiological parameter derivation module.

* * * * *